United States Patent [19]
Ishihara et al.

[11] Patent Number: 5,331,093
[45] Date of Patent: Jul. 19, 1994

[54] ANTI-FOCOSYLCERAMIDE MONOCLONAL ANTIBODY

[75] Inventors: Hideki Ishihara, Saitama; Hiroshi Hattori, Tokyo; Kenichi Ono, Saitama, all of Japan

[73] Assignee: Hoechst Japan Limited, Tokyo, Japan

[21] Appl. No.: 888,306

[22] Filed: May 27, 1992

Related U.S. Application Data

[63] Continuation of Ser. No. 432,898, Nov. 7, 1989, abandoned.

[30] Foreign Application Priority Data

Nov. 9, 1988 [JP] Japan .................................. 63-281433

[51] Int. Cl.$^5$ .................. C07K 15/28; G01N 33/574; C12N 5/12
[52] U.S. Cl. .............................. 530/387.5; 530/388.1; 530/388.8; 435/7.23; 435/240.27
[58] Field of Search ............... 530/388.1, 388.8, 387.5; 435/240.27, 172.2, 70.21, 7.23

[56] References Cited
PUBLICATIONS

Campbell, A. M., Monoclonal Antibody Technology, Chapters 1 ands 2, pp. 1-65, 1985.
Yoshino, et al., Biochemistry, 21:928-934, 1982.

Primary Examiner—Paula Hutzell
Assistant Examiner—Susan A. Loring
Attorney, Agent, or Firm—Finnegan, Henderson, Farabow, Garrett & Dunner

[57] ABSTRACT

The invention relates to a monoclonal antibody PC47H specifically recognizing fucosylceramide derived from a ceramide-mono-glycoside fraction of neutral glycolipid extracted and purified from human cancer tissues and having properties such as belonging to IgM and showing reactivity to neither of normal peripheral blood lymphocyte, normal erythrocyte, normal fibroblast nor cell lines derived from leukemia, hepatoma, breast cancer and neuroblastoma but to cell lines derived from lung cancer, stomach cancer, colon cancer and pancreas cancer; a hybridoma having ability to produce the aforementioned monoclonal antibody; a method for manufacturing the aforementioned monoclonal antibody which comprises immunizing an animal with a neutral glycolipid fraction extracted from human pancreas cancer, fusing animal cells with myeloma cells to generate hybridomas, cloning the hybridomas, selecting clones which produce monoclonal antibodies which specifically recognize fucosylceramide and then using the clones to manufacture the monoclonal antibody; and a diagnostic aid of cancers such as lung cancer, stomach cancer, colon cancer and pancreas cancer containing the aforementioned monoclonal antibody as an active component.

2 Claims, 2 Drawing Sheets

I  CERAMIDE-MONO-GLYCOSIDE
II  CERAMIDE-DI-GLYCOSIDE
III  CERAMIDE-TRI-GLYCOSIDE
IV  CERAMIDE-TETRA-GLYCOSIDE
     DEVELOPING SOLVENT  CMW 65:30:6
 COLORING
A :  ORCINOL-HYDROCHLORIC ACID REAGENT
     (WHOLE NEUTRAL GLYCOLIPID FRACTION)
B :  TLC-IMMUNOSTAINING WITH PC47H

ANTI-FOCOSYLCERAMIDE MONOCLONAL ANTIBODY

This application is a continuation of application Ser. No. 07/432,898, filed Nov. 7, 1989, now abandoned.

BACKGROUND OF THE INVENTION

This invention relates to a novel monoclonal antibody effective for the diagnosis of human cancers, a hybridoma producing the antibody; a method for manufacturing the antibody and a diagnostic aid using the antibody.

The present invention provides a monoclonal antibody which reacts specifically with fucosylceramide of a ceramide-mono-glycoside fraction contained in neutral glycolipid extracted from human cancer tissues, a hybridoma which produces the antibody, a method for manufacturing the antibody by using the hybridoma and a diagnostic aid using the antibody.

Since a monoclonal antibody preparation technique was established in 1975 by Köhler and Milstein [Nature 256:495 (1975)], numerous investigators have tried to prepare a monoclonal antibody which specifically recognizes cancer tissues up to now. They employed a method of selecting a hybridoma, which is unreactive with human normal cells but recognizes human cancer cells by directly immunizing a mouse with the human cancer cells. It turned out that many of the tumor antigens which were recognized by the monoclonal antibody obtained by the above-described method were sugar chain antigens [S. Hakomori, Scientific American 254, 32.41 (1986)].

As typical examples thereof, CA-19-9, sialyl SSEA-1, etc. can be mentioned. They have been already used widely in the clinical field as a marker of cancer [Reiji Kannagi, Clinical Pathology XXXTV: 11, 1247~1264 (1986)]. However, these antigens have sugar chains carrying 5 or more sugars. With respect to a short-sugar chain antigen, it is considered that the research thereon is still insufficient although their ability of being important tumor-antigens has been discussed already.

Fucosylceramide (structural formula: L-Fuc$\alpha$-1Cer) composed of one fucose being linked to ceramide (lipid-part) was isolated from colon cancer tissues by Senitiroh Hakomori et al in 1976 and there was a chance that the fucosylceramide was glycolipid which was expressed specifically in human cancers [JBC, 251, 2385~2387 (1976)]. In addition, they immunized a rabbit with chemically synthesized fucosylceramide to prepare a polyclonal antibody. However, this polyclonal antibody was not specific to fucosylceramide alone but cross-reactive to ceramide and galactosylceramide, so that it was impossible to accurately determine the presence of fucosylceramide in human cancer cells or tissues [Biochemistry, 21, 928~934 (1982)].

SUMMARY OF THE INVENTION

As described above, a monoclonal antibody reacting specifically with fucosylceramide has not been known yet. If there is a monoclonal antibody specifically recognizing fucosylceramide, it would not only be useful for the diagnosis of human cancers but also very useful for the determination of fucosylceramide in human cancer cells or tissues.

In our intensive research on a monoclonal antibody reacting specifically with fucosylceramide, we proved that the monoclonal antibody PC47H which was produced from a hybridoma established by immunizing a mouse with a neutral glycolipid fraction extracted from a human pancreas cancer tissue specifically reacted with fucosylceramide and found that it was possible to determine the presence of fucosylceramide in various cancer cells by using the antibody according to the invention.

The present invention therefore relates to:

(1) A monoclonal antibody specifically recognizing fucosylceramide.

(2) A monoclonal antibody according to (1) having the following properties:
a. Ig class: IgM
b. Reactive with cell lines derived from lung cancer, stomach cancer, colon cancer and pancreas cancer.
c. Unreactive with normal peripheral blood lymphocyte, normal erythrocyte and normal fibroblast.
d. Unreactive with cell lines derived from leukemia, hepatoma, breast cancer and neuroblastoma.

(3) A monoclonal antibody according to (1) which is named PC47H.

(4) A hybridoma having ability to produce a monoclonal antibody according to (1), (2) or (3).

(5) A method for manufacturing a monoclonal antibody according to (1), (2) or (3) by immunizing an animal with a neutral glycolipid fraction extracted from human pancreas cancer, fusing animal cells with myeloma cells to generate hybridomas, cloning the hybridomas, selecting clones producing monoclonal antibodies specifically recognizing fucosylceramide and isolating the monoclonal antibody.

(6) A diagnostic aid for the determination of cancers which contains a monoclonal antibody according to (1), (2) or (3) as an active component.

(7) A diagnostic aid according to (6) effective for lung cancer, stomach cancer, colon cancer and pancreas cancer.

According to the present invention, a monoclonal antibody which is useful for the accurate determination of the presence of fucosylceramide in various cancer tissues and cells is provided. In addition, a diagnostic aid which is effective for the diagnosis of cancers is provided by using this monoclonal antibody.

DETAILED DESCRIPTION OF THE INVENTION

Figure 1:
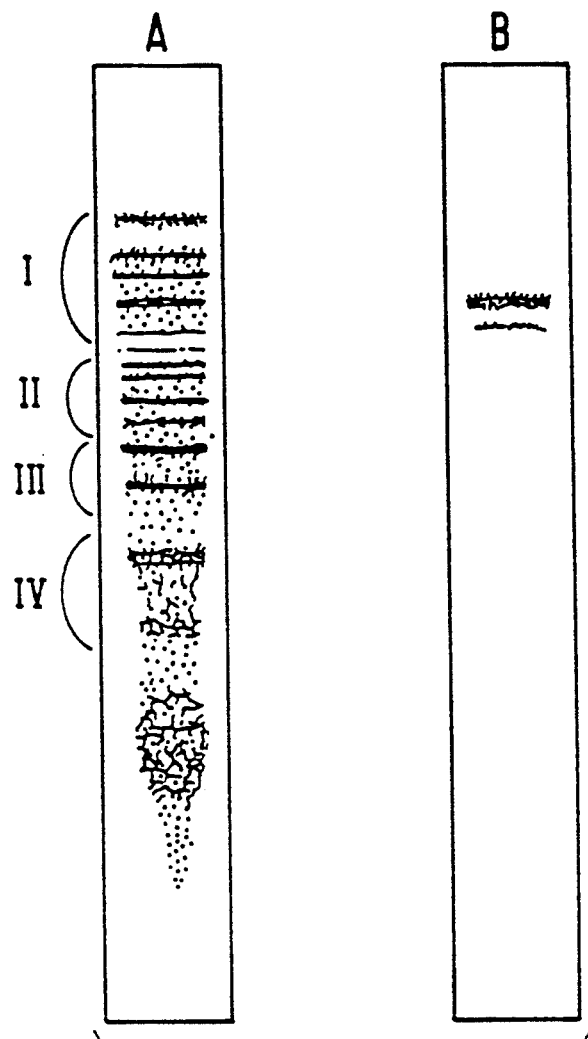
FIG. 1A shows a TLC (Thin Layer Chromatography) pattern by staining of all neutral glycolipid fractions.
FIG. 1B shows a TLC pattern by immunostaining of fucosylceramide (Fuc-Cer) with monoclonal antibody PC47H.

Hereinafter, the present invention will be described in detail.

A mouse is immunized with a neutral glycolipid fraction extracted from human pancreas cancer tissues [immunization was carried out according to the method of Carlson et al {Eur. J. Immunol., 16, 951 (1986)}. Spleen cells of the mouse are fused with mouse myeloma cells to prepare hybridomas. Then, the hybridomas are cloned by limited dilution to obtain a monoclonal antibody [J. Biochem (Tokyo), 99, 269 (1986)]. An antigen recognizing the monoclonal antibody is analyzed [J.

Immunol. Methods, 38, 85 (1980)] by immunological staining using thin layer chromatography (TLC) (hereinafter abbreviated to TLC-immunostaining) [Can. Res., 47, 1968 (1987)] and by enzyme immunoassay (EIA) using a microtitration-plate to which glycolipid is adsorbed.

The monoclonal antibody produced by the above-described hybridoma belongs to IgM class and specifically recognizes fucosylceramide which occurs in a ceramide-mono-glycoside fraction of neutral glycolipid as an antigen. A specific example of the present monoclonal antibody is PC47H which is produced by a hybridoma cell line FERM BP-2557 which was deposited at Fermentation Research Institute, 1-3 Higashi 1-chome, Tukuba-shi, Ibaraki-ken, 305 Japan, on Nov. 4, 1988.

Hereinafter, a method for manufacturing the present monoclonal antibody will be described in detal.

(1) Preparation of Neutral Glycolipid

A human pancreas cancer tissue is cut into small pieces by using a Warring blender or the like. The tissue pieces are extracted with a 2:1 mixture of chloroform-methanol (hereinafter abbreviated to C-M 2:1), a 1:1 mixture or chloroform-methanol (hereinafter abbreviated to C-M 1:1) and a 1:2:0,8 mixture of chloroform-methanol-water (hereinafter abbreviated to C-M-W 1:2:0,8), each volume of which is approx. 20 times that of the tissue pieces. The extract is evaporated to dryness under reduced pressure to obtain total lipid fractions. Then, the total lipid fractions are dissolved in C-M 1:1 containing 0,5N KOH. After leaving the mixture overnight at room temperature, the resulting solution is dialyzed against distilled water to remove a phospholipid fraction. This fraction is dissolved in C-M-W 30:60:8 and then loaded on a DEAE-Sephadex A-25 (acetic acid type, manufactured by Pharmacia Fine Chemicals Inc.) to adsorptively remove acidic lipid fractions. Whereby, neutral lipid fractions are loaded on a Silica Gel 60 (manufactured by Merck Corp.) column to firstly elute simple lipids with chloroform and then elute a crude glycolipid fraction with C-M-W 65:30:8. After evaporating to dryness the crude glycolipid fraction is acetylated by dissolving the same in a 3:2 mixture of pyridine-acetic anhydride. The acetylated fraction is loaded on a Florisil (manufactured by Floridin Inc.) column After eluting low polar lipids with 1,2-dichloroethane, an acetylated glycolipid fraction is eluted with a mixture of 1,2-dichloroethane-acetone (1:1). This fraction is dissolved in a 1:4 mixture of 28% ammonia water-methanol and then allowed to stand for 12 hours at room temperature to deacetylate the same.

For the analysis of a neutral glycolipid fraction, thin layer chromatography (TLC) is adopted. In the TLC, a Silica Gel 60 plate (5461 or 5547, manufactured by Merck Corp.) is used, which is developed with C-M-W 65:25:4. For the dectection of neutral glycolipid, resorcinol reagent is used.

The determination of glycolipid is performed by gas liquid chromatography.

(2) Preparation of Immunized Mouse Spleen Cells

An adequate amount of glycolipid prepared as in (1), 5 mg of lipid A, 68 mg of dimyristyl phosphatidyl cholin, 28 mg of cholesterol and 6 mg of dicetylphosphate are dissolved in a suitable organic solvent. After evaporating the mixture to dryness in a 50-ml eggplant-shape flask, 10 ml of phosphate buffer solution (PBS; containing 2.8 g of dibasic sodium phosphate, 0.3 g of monobasic sodium phosphate, 9 g of NaCl and 1 l of distilled water; pH 7.2) and 3 ml of glass beads (2 mm diameter) are added to the dried mixture. The resulting solution is strongly shaken and stirred to form liposome. The suspension, without the glass beads is administered to approximately 8 week old mice hypodermically (in the joint parts of the limbs) in a volume of 150 µl and intraperitoneally in the volume of 50 µl to give a total volume of 200 µl to immunize them. Thereafter, immunization is repeated in 2-week intervals in the same manner as aforementioned. Antiserum is collected from the fundus venous plexus every 1 week and its antibody titer is determined by enzyme immunoassay.

ENZYME IMMUNOASSAY

Neutral glycolipid prepared as in (1) is dissolved in C-M 2:1 and then mixed in a adequate amount of ethanol (this solution is so adjusted to contain 20 to 100 ng/ml of glycolipid). The resulting solution is dispensed at 50 µl/well into a 96-well EIA plate (manufactured by Sanko Junyaku Co., Ltd.) and allowed to stand for 1 hour at 56° C. to evaporate ethanol. Then, each well is filled with 1% bovine serum albumin (BSA)-PBS (hereinafter abbreviated to BSA/PBS) and allowed to stand for 1 hour at room temperature to block nonspecific adsorption. Then, the BSA/PBS is discarded and a BSA/PBS-diluted specimen (mouse antiserum or hybridoma culture supernatant) is dispensed at 50 µl/well and incubated for 1 hour at room temperature. After washing each well 3 times with BSA/PBS, a 2,000-fold-dilution of peroxidase-linked rabbit anti-mouse IgG (manufactured by DAKO Inc.) is dispensed in 50 µl/well as a second antibody and allowed to stand for 1 hour at room temperature. After washing the wells 3 times with BSA/PBS, an OPD substrate solution (a solution prepared by first dissolving 10 mg of o-phenylenediamine in 10 ml of citrate buffer solution (pH 5,0) and then immediately before the use adding an aqueous solution of hydrogen peroxide to give the final concentration of 0,006%) is dispensed into the wells at 50 µl/well and incubated for 20 to 30 minutes at room temperature. Then, 50 µl of 2M sulfuric acid is added to each well to stop the reaction. The absorbance at 490 nm is measured by using an photometer.

A mouse carrying antiserum which strongly reacts with the immunogen is selected according to the above determination methods and used for the preparation of a hybridoma. Then, a spleen is sterilely removed from the immunized mouse to which the immunogen is boostered 3 days prior to cell fusion. The spleen is broken up into single cells by using a homogenizer. The single cells are washed thoroughly with an RPMI 1640 medium not containing fetal bovine serum (manufactured by Nippon Suisan Kaisha, Ltd.) and then used as fusion spleen cells.

(3) Preparation of Myeloma Cell

As a myeloma cell, mouse-derived 8-azaguanine resistant myeloma cell line P3-X63 Ag8-U1(P3-U1) [Current Topics in Microbiology and Immunology 1 and European J. Immunology, 6, 511~519 (1976)] is used. Prior to the day of fusion, the myeloma cells are incubated for several days in the presence of 8-azaguanine to completely remove revertants. The myeloma cells are so prepared that the cells in logarithmic growth phase can be used in the number of $2 \times 10^7$ or more.

(4) Cell Fusion

The spleen cells of an immunized mouse prepared as in (2) and myeloma cells obtained as described in (3) are thoroughly washed with an RPMI 1640 medium not containing fetal bovine serum and then so mixed that the cell number ratio of the immunized spleen cell to the myeloma cell is 10 to 1. After centrifuging the mixture (at 1,200 rpm for 5 min.), the supernatant is discarded. After loosening the precipitated cell cluster thoroughly, 1 ml of polyethylene glycol solution (RPMI 1640 medium containing 40% polyethylene glycol 1540 manufactured by Wako Junyaku Co., Ltd.) previously heated to 37° C. is added thereto. After centrifuging the resulting solution successively at 300 rpm for 2 min., 700 rpm for 2 min. and 1,000 rpm for 2 min., the supernatant is removed and a HAT medium (RPMI 1640 medium containing hypoxanthine, thymidine, aminopterin and 15% fetal bovine serum), is added to the pellet, followed by gently suspending cells with a pipette. This suspension is dispensed at 200 $\mu$l/well into a 96-well plate and incubated for 7 days in a $CO_2$ incubator. Then, 100 $\mu$l of culture supernatant is discarded and an equal volume of HAT medium is freshly added to the wells. After continuing the same operations in 2 to 3 day intervals for 3 weeks from the day of fusion, the medium is gradually changed to HT medium (a medium prepared by excluding aminopterin from the HAT medium). From wells in which hybridomas are proliferating, the culture supernatant is partially sampled and subjected to the determination of its antibody titer against the neutral glycolipid fraction used as an immunogen according to the above described enzyme immunoassay.

Hybridomas showing high antibody titer are subjected to cloning according to limiting dilution by using a thymocyte of a mouse aged approximately 4 weeks as a feeder cell and an RPMI 1640 medium containing 15% fetal bovine serum as a dilution.

(5) Preparation of Monoclonal Antibody

There are two ways of preparation, that is one way in which the culture supernatant of hybridomas, producing monoclonal antibodies, is used directly and another way in which a large quantity of purified monoclonal antibodies is used. In the latter approx. $1 \times 10^6$ cells of each hybridoma producing the aimed antibody are intraperitoneally administered to mice previously pretreated with pristane, ascites is collected from mice showing ascitic cancer after approx. 2 weeks, the ascites is centrifuged (at 3,000 rpm for 10 min.) and then the supernatant is cryopreserved under $-70°$ C.

In case of purifying an antibody from this ascites, the ascites is salted out with 45% saturated ammonium sulfate 3 times at 4° C. and then gel-filtrated by using Sephacryl S300 (manufactured by Pharmacia Fine Chemicals, Inc.). In case of the isotype of antibody being IgM, the antibody is gel-filtrated by using a phosphate buffer solution containing 0,5M sodium chloride. The determination of protein concentration is performed by using a protein assay kit manufactured by Bio-Rad Laboratories, Inc.

The determination of the isotype of an antibody is performed according to Ouchterlony technique (double immunodiffusion technique) by using rabbit antisera specific to each isotype (manufactured by Miles, Inc.).

(6) Immunostaining Method Using Thin-layer Chromatography (TLC-Immunostaining Method)

As a thin-layer plate, a Silica Gel 60 plate (5547, manufactured by Merck Corp.) is used. Neutral glycolipid fractions extracted from various cancers and normal tissues are developed by using a developing solvent C-M-W 65:30:6. The thin layer plate is dried thoroughly, immersed in 5% BSA/PBS and then allowed to stand for 1 hour at room temperature to block the reaction of non-specific antibodies.

After removing the 5% BSA/PBS by aspiration, the plate is immersed in the culture supernatant of the positive hybridomas obtained as in (4) and then allowed to stand for 3 hours at room temperature. After washing the plate 5 to 8 times with 0.5% BSA/PBS, a 100-fold dilution of biotinized anti-mouse IgG (manufactured by DAKO, Inc.) is added thereto and reacted for 1 hour at room temperature. Then, the plate is washed 5 to 8 times with 0.5% BSA/PBS.

Then, an avidin coupled peroxidase solution (manufactured by Funakoshi Co., Ltd.) which is previously prepared is added to the plate and reacted for 1 hour at room temperature. After washing the resulting plate 5 to 8 times with 0.5% BSA/PBS and then twice with PBS, a substrate solution (IMMUNOSTAIN ® manufactured by Konica Corp.) is added thereto and reacted for 20 to 30 minutes at room temperature with slight shaking. After washing 2 to 3 times with 0.5% BSA/PBS, the plate is air-dried. Then, the location of an antigen to be recognized by the monoclonal antibody contained in the culture supernatant is identified on the thin-layer plate.

Hereinafter, the present invention will be described, in examples. However, the present invention shall not be restricted to the examples.

EXAMPLE 1

(1) Preparation of Neutral Glycolipid

From 25,8 g of human pancreas cancer tissues, a neutral glycolipid fraction was extracted and purified according to the aforementioned general method. The total quantity of neutral glycolipid obtained was 3,74 mg. The development pattern of this neutral glycolipid fraction obtained by using a thin-layer plate (5547, manufactured by Merck Corp.) is shown in FIG. 1-A.

(2) Preparation of Immunized Mouse Spleen Cells

The neutral glycolipid fraction obtained from a human pancreas cancer tissue in the manner described in (1) was administered to 8-week old mice at 25 $\mu$g (in terms of glycolipid)/mouse to immunize according to the aforementioned method. Thereafter, the mice were further immunized 5 times with 25 $\mu$g (in terms of glycolipid/mouse) of the same antigen at intervals of 2 weeks. The one having the highest antibody titer of its antiserum among these immunized mice was selected by enzyme immunoassay. From this mouse, spleen cells were taken and then subjected to cell fusion.

(3) Preparation of Mouse Myeloma Cell 8-azaguanine-resistant mouse myeloma cell line P3-U1 was cultured in an FCS RPMI 1640 medium containing 15% fetal bovine serum. At the time of cell fusion, approx. $2 \times 10^7$ cells were used for cell fusion.

(4) Preparation of Hybridoma

Spleen cells and myeloma cells obtained as in (2) and (3) respectively were mixed in a 10:1 ratio to undergo cell fusion according to the foregoing method.

Each culture supernatant was sampled from wells in which hybridomas were proliferating and then subjected to aforementioned enzyme immunoassay to measure its antibody titer. Then, wells having high titers were selected and subjected to the cloning to establish a hybridoma PC47H.

(5) TLC-Immunostaining Method

In order to detect an antigen which is recognized by a monoclonal antibody produced by the obtained hybridoma cell line, the TLC-immunological staining was performed by using a Silica Gel 60 plate (5547, manufactured by Merck Corp.).

As a result, a monoclonal antibody PC47H which was reactive to the ceramide-mono-glycoside fraction contained in the neutral glycolipids extracted from a human pancreas cancer tissue was obtained.

A reaction pattern of PC47H according to TLC-immunological staining method is shown in FIG. 1-B.

The PC47H monoclonal antibody (mab) did not show reactivity with any fractions other than the ceramide-mono-glycoside fraction of neutral glycolipids.

(6) Isotype of PC47H mab

By the use of rabbit antisera (manufactured by Miles Inc.) specific to each mouse immunoglobulin Ig classes, the isotype of the PC47H was determined by double immunodiffusion. As the result, it became clear that the monoclonal antibody PC47H belonged to IgM class. The hybridoma producing anti-fucosylceramide monoclonal antibody PC47H prepared according to the present invention is deposited in Fermentation Research Institute, Agency of Industrial Science and Technology, 1-3 Higashi 1-chome, Tukuba-shi, Ibaraki-ken, 305 Japan, with the accession under FERM BP-2557, (date of deposit Nov. 4, 1988).

EXAMPLE 2

A fraction of ceramide-mono-glycoside in mammal contains galactosylceramide (hereinafter abbreviated to "Gal-Cer"), glucosylceramide (hereinafter abbreviated to "Glc-Cer") and fucosylceramide (hereinafter abbreviated to "Fuc-Cer"), as reported previously [Akira Makita, "Methods of Studying Complex Glycolipid II", pp. 3~12 in "Lectures on Biochemical Experiment, 2nd series", Vol. 4, Tokyokagakudojin, Tokyo (1986)].

In order to identify the antigen to be recognized by PC47H, we carried out the following experiment.

The authentic Gal-Cer (manufactured by Seikagaku Kogyo K. K.) and purified Glc-Cer and chemically synthesized Fuc-Cer were separately dissolved in a solvent of chloroform/methanol (CM), 2:1 by volume, and the solvent was replaced with ethanol. The resulting ethanol solution was dispensed into wells of an ELISA plate (manufactured by SANKO JUNYAKU Co., Ltd.) at 80, 40, 20, 10 and 5 ng/well and then allowed to stand overnight at room temperature to evaporate the solvent.

After blocking the wells with BSA/PBS, the supernatant of PC47H culture was dispensed at 50 μl/well and then reacted for 2 hours at room temperature.

After washing the wells 3 times with BSA/PBS, a 2,000-fold dilution of peroxidase-linked rabbit anti-mouse immunoglobulin antibody (manufactured by DAKO Inc.) was dispensed at 50 μl/well and then allowed to stand for 1 hour at room temperature.

Figure 2:
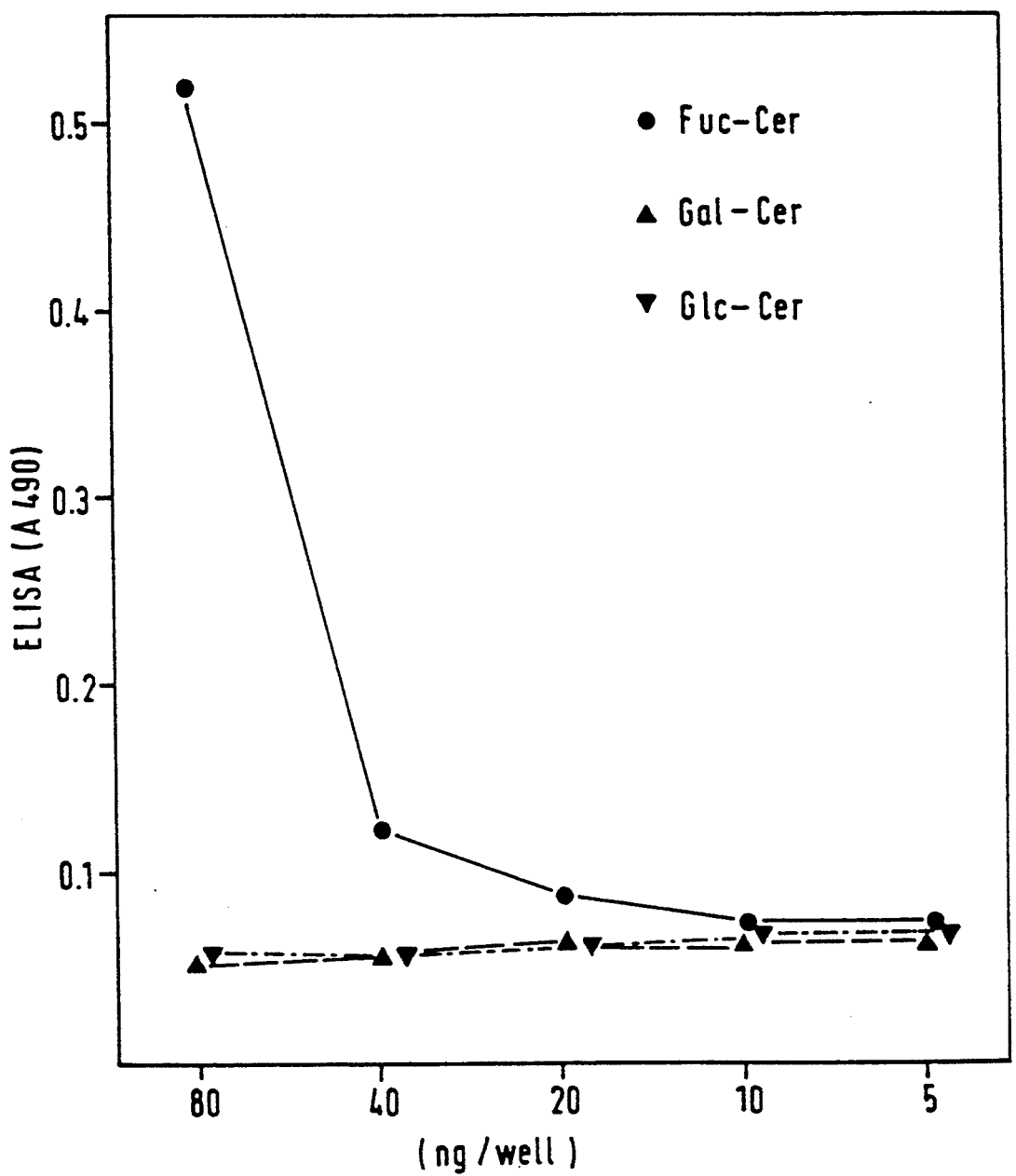
FIG. 2 shows the results of the analysis of crossreactivity of monoclonal antibody PC47H of Fuc-Cer, Gal-Cer, and Glc-Cer.

After washing each well 3 times with BSA/PBS, the aforementioned OPD substrate solution was added to each well. After a 20-minute reaction at room temperature, the reaction was stopped with 50 μl of 2M sulfuric acid. The absorbance at 490 nm of the solution was measured by an photometer. The results are shown in FIG. 2.

The PC47H mab showed no cross-reactivity at all to Gal-Cer or Glc-Cer but significantly reacted to Fuc-Cer alone. This result proves that the PC47H is a monoclonal antibody specifically reacting with Fuc-Cer which is present in the ceramide-mono-glycoside fraction of neutral glycolipids.

EXAMPLE 3

The reactivity of the anti-fucosylceramide monoclonal antibody PC47H to various cell lines was examined according to the following EIA method.

That is, cells were suspended in an RPMI 1640 culture medium containing 15% of FCS and were supplied to a 96-well filtration plate (millititer GV, manufactured by Millipore Inc.) at the rate of $10^4$ cells/well and then allowed to stand for 1 hour at 37° C. (the reaction of nonspecific binding is blocked by this operation). After removing culture media from the wells by aspiration, the supernatant of PC47H culture was dispensed at 100 μl/well and then reacted for 1 hour at 4° C.

After washing the resulting cells 3 times with "PBS for cell" (dibasic sodium phosphate 2.9 g, monobasic potassium phosphate 0,2 g, potassium chloride 0,2 g, NaCl 8 g and distilled water 1 l; pH 7,2), a 2,000-fold dilution of peroxidase-linked rabbit anti mouse immunoglobulin antibody was added thereto at the rate of 100 μl/well and then reacted for 1 hour at 4° C. After washing each well 3 times with "PBS for cell", an OPD substrate solution was added thereto at the rate of 100 μl/well to carry out reaction with the washed cells.

The enzymatic reaction was continued for 20 minutes and then stopped by adding 2M sulfuric acid at the rate of 50 μl/well. The degree of coloring was judged by using a photometer. The results are given in Table 1.

The anti-fucosylceramide monoclonal antibody PC47H showed reactivity with cell lines derived from lung cancer, stomach cancer, colon cancer and pancreas cancer. However, the PC47H did not show reactivity with normal peripheral blood lymphocyte, normal erythrocyte or normal fibroblast. In addition, the PC47H mab did not show reactivity with cell lines derived from leukemia, hepatoma, breast cancer or neuroblastoma either.

TABLE 1

| Reactivity of Monoclonal Antibody PC47H to Various Cells according to Enzyme Immunoassy (EIA) Using the Cells | |
|---|---|
| Name of Cell | PC47H |
| Leukemia cell line | 0/6*1 |
| Lung cancer cell line | 2/3 |
| Stomach cancer cell line | 1/1 |
| Colon cancer cell line | 2*2/2 |
| Pancreas cancer cell line | 3*3/3 |
| Hepatic cancer cell line | 0/1 |
| Neuroblastoma cell line | 0/1 |
| Breast cancer cell line | 0/1 |
| Normal fibroblast cell line | 0/1 |
| Normal peripheral blood lympocyte | 0/3 |
| Normal erythrocyte | 0/3 |

*1 Number of positive cases/Number of cell line or specismen.
*2 2 cases were both weakly positive.
*3 One case out of 3 was weakly positive and the 2 remaining cases were positive.

What is claimed is:

1. A monoclonal antibody which is PC47H as produced by the hybridoma deposited under international deposit number FERM BP-2557.

2. A diagnostic acid for lung, colon or stomach cancer, said diagnostic acid comprising a monoclonal antibody as claimed in claim 1 and a carrier.

* * * * *

UNITED STATES PATENT AND TRADEMARK OFFICE
CERTIFICATE OF CORRECTION

PATENT NO. : 5,331,093
DATED : July 19, 1994
INVENTOR(S) : Hideki Ishihara et al.

It is certified that error appears in the above-indentified patent and that said Letters Patent is hereby corrected as shown below:

Claim 2, column 8, line 64 change "acid" to --aid--.
On the title page: Item [54] and Column 1, line 1
change "ANTI-FOCOSYLCERAMIDE" to --ANTI-FUCOSYLCERAMIDE--.

Signed and Sealed this

Fourteenth Day of March, 1995

Attest:

BRUCE LEHMAN

Attesting Officer

Commissioner of Patents and Trademarks